US005607857A

United States Patent [19]

Grossman et al.

[11] Patent Number: 5,607,857
[45] Date of Patent: Mar. 4, 1997

[54] RHODOCOCCUS SPECIES FOR REMOVING SULFUR FROM ORGANIC CARBONACEOUS FUEL SUBSTRATES-(LAW295)

[75] Inventors: Matthew J. Grossman, Flemington; Mary K. Lee, Somerville, both of N.J.; James D. Senius, Easton, Pa.; Robert L. Burghoff, West Ford, Mass.; David L. Elmendorf, Edmond, Okla.

[73] Assignee: Exxon Research and Engineering Company, Florham Park, N.J.

[21] Appl. No.: 489,859

[22] Filed: Jun. 13, 1995

Related U.S. Application Data

[63] Continuation-in-part of Ser. No. 284,773, Aug. 2, 1994, abandoned, which is a continuation of Ser. No. 106,480, Aug. 13, 1993, abandoned, which is a continuation of Ser. No. 898,647, Jun. 15, 1992, abandoned.

[51] Int. Cl.$^6$ ............................................. C10G 32/00
[52] U.S. Cl. ......................... 435/282; 435/262.5; 435/281
[58] Field of Search ............................. 435/281, 282, 435/262.5, 822, 252.1

[56] References Cited

PUBLICATIONS

Zurrer et al., Applied and Environmental Microbiology, 1987, 53:1459–1463.
Ching et al., Energy Research Abstracts, 1989, 14(16) Abstract No. 33212.

*Primary Examiner*—Leslie Wong
*Attorney, Agent, or Firm*—Ronald D. Hantman

[57] ABSTRACT

A process is provided for removing organic sulfur from a sulfur-containing organic carbonaceous fuel substrate such as coal or petroleum products having sulfur-carbon bonds. The process comprises contacting the substrate with a microorganism having all the identifying characteristics of Rhodococcus species ATCC 55309 or ATCC 55310 which cleaves the sulfur-carbon bonds resulting in the removal or the organic sulfur from the substrates.

6 Claims, 1 Drawing Sheet

RHODOCOCCUS SPECIES FOR REMOVING SULFUR FROM ORGANIC CARBONACEOUS FUEL SUBSTRATES-(LAW295)

This is application is a continuation-in-part of Ser. No. 08/284,773, filed Aug. 2, 1994, now abandoned, which is a continuation of Ser. No. 08/106,480, filed on Aug. 13, 1993, now abandoned, which is a continuation of Ser. No. 07/898,647, filed on Jun. 15, 1992 now abandoned.

BACKGROUND OF THE INVENTION

This invention relates to two pure strains of bacteria capable of selective removal of organically bound sulfur from carbonaceous materials while maintaining the calorific value of the carbonaceous materials. The microorganisms of this invention are particularly useful in removal of organic sulfur from fossil fuels such as oils and coals.

Conventional methods for the removal of organic sulfur from fuels rely on heterogeneous catalysis which is limited by the range of compounds which can be successfully removed. Aromatic sulfur containing compounds make up a significant percentage of the organic sulfur in fuels and these are generally the least susceptible to removal by conventional methods. The most recalcitrant of the aromatic sulfur-containing compounds are those in which the sulfur atoms are sterically hindered.

Most microbial methods described to date for the removal of sulfur from petroleum products, coal, tar sands and shale oil are limited to inorganic sulfur. The majority of the microbial methods involving organic sulfur removal are non-specific in that they attack the carbon skeletons of the organic constituents, thus resulting in a high degree of unwanted side reactions and reduction of the calorific value of the fuel. In addition, there have been no reports on the selective removal of sulfur from those organic constituents in which the sulfur atoms are sterically hindered.

The following is a brief description of the prior art.

Sulfur in carbonaceous fuels is undesirable due to its ability to promote corrosion in storage and processing equipment and, when the fuel is combusted, the release of sulfur oxide gases which are attributed to detrimental affects on the environment. Sulfur is found in two forms in these materials: 1) inorganic, with the principle forms being elemental sulfur, sulfate, and pyrite; and 2) organic sulfur, with the principle forms in crude oils being (Rall, H. T., Thompson, C. J., Coleman, H. J., and Hopkins, R. L. (1972) Sulfur compounds in crude oil. U.S. Department of the Interior, Bureau of Mines, Bulletin 659) aliphatic and aromatic thiols, dialkyl, diaryl, alkyl-aryl and cyclic sulfides, disulfides, and thiophenes such as thiophene, benzothiophene, dibenzothiophene and various derivatives of these compounds to which alkyl and/or aryl groups are attached. Although the structure of coal is not known the sulfur forms are believed to be similar to oils except that they are covalently bound in the complex coal matrix.

Coal can contain appreciable quantities of both forms of sulfur with a total sulfur content, typically between 1 and 4%, but in some cases being greater than 11% (Chakrabarti, J. N. (1978) Analytical Methods for Coal and Coal Products, 1,279–322. New York: Academic). The sulfur content of crude oils varies widely ranging from less than 0.1% to 5% and more in some of the heavy crudes (International Petroleum Encyclopedia. (1983) Penn Well Publishing Co., Tulsa, Okla.). In crude oils sulfur is also found in both inorganic and organic forms, in addition, hydrogen sulfide may also be present. In distillate fractions of crude oils the sulfur content increases with the boiling range of the fraction with the bulk of the sulfur found in the middle distillates fractions and above.

A number of processes have been developed to remove inorganic sulfur forms from coal including oxidation to sulfur oxide gases and reduction to hydrogen sulfide gas, and physical cleaning by froth flotation and upward current classifiers based on the substantial difference in density of coal and pyrite. In addition, a number of microbial approaches have been developed which rely largely on the oxidation of pyrite and reduced sulfur forms, including elemental sulfur, by Thiobacillus specia and Sulfolobus species, releasing sulfur in the form of sulfuric acid and sulfates (reviewed in: Bos, P., and Kuenen, J. G. (1990) Microbial treatment of coal. In: Microbial Mineral Recovery (Ehrlich, H. L., and Briedey, C. L. eds) McGraw Hill, New York, pp. 343–377). Some of the microbial process have been patented, exemplified by Detz, C. M., and Barvinchak, G. (1978) U.S. Pat. No. 4,206,288 in which *Thiobacillus ferroxidans* is employed in a slurry reactor design to remove inorganic sulfur from coal, and Attia, Y. A. and Elzeky, M. A. (1988) U.S. Pat. No. 4,775,627 in which *Thiobacillus ferroxidans* is used in conjunction with physical separation to remove inorganic sulfur.

The removal of organic sulfur is more problematic. In coal organic sulfur is covalently bound within the complex carbonaceous structure. For precombustion sulfur removal this requires that the coal matrix be exposed to the desulfurizing agent by depolymerization and/or solubilized prior to treatment. Once pretreated in this way the organic sulfur in the coal product is removed by similar techniques as those used for oils. The requirement for pretreatment is a major factor in determining costs for a coal desulfurization process. Alternatively, organic sulfur in coal is removed by scrubbing of sulfur dioxide after combustion. The use of scrubbers typically limits the use of coal to large facilities were their use is economically feasible (Bos, P., and Kuenen, J. G. (1990) Microbial treatment of coal. In: Microbial Mineral Recovery (Ehrlich, H. L., and Brierley, C. L., eds) McGraw-Hill, New York, pp. 343–377).

In standard refinery operations organic sulfur in oils is removed by hydrodesulfurization using heterogeneous inorganic catalysts, high temperature and high hydrogen pressure. These methods are effective in removing thiols, most sulfides and disulfides but are much less effective against thiophenic sulfur, particularly the dibenzothiophenes containing substitutions rendering the sulfur atom sterically hindered, i.e., monobeta and dibeta substituted dibenzothiophenes. Tighter regulations on the maximum mount of sulfur allowable in fuels will necessitate the removal of even the most recalcitrant sulfur compounds. This requires the development of new technologies or the processing of fuels under much more severe conditions, i.e., increased temperature and hydrogen pressure, thereby greatly increasing the cost of fuel processing.

A large amount of research and many patents have been issued on the use of microorganisms to remove organic sulfur from coal and oils (reviewed in: 1) Bos, P. and Kuenen, J. G. (1990) Microbial treatment of coal. In: Microbial Mineral Recovery (Ehrlich, H. L., and Brierlcy, C. L., eds) McGraw-Hill, New York, pp. 343–377:2) Foght, J. M., Fedorak, P. M., Gray, M. R., and Westlake, D. W. S. (1990) Microbial desulfurization of petroleum. In: Microbial Mineral Recovery (Ehrlich, H. L., and Brierley, C. L., eds) McGraw-Hill, New York, pp. 379–407). The majority of this work has focused on aerobic processes using dibenzothiophene as the model compound to isolate organisms and evaluate reaction mechanisms. Research on the use of anaerobic bacteria to remove sulfur via a reductive process resulting in the release of sulfur as hydrogen sulfide is exemplified by Kim, B. H., Kim, T. S., and Kin, H. Y. (1990) U.S. Pat. No. 4,954,229, in which electrical energy is used to supply reducing power for the reduction or organic sulfur by Desulfovibrio species.

The vast majority of microorganisms isolated which can degrade dibenzothiophene aerobically do so by the initial oxidation and cleavage of one of the aromatic rings, and in so doing initiate the complete degradation of the molecule to $CO_2$, $H_2O$ and $SO_4=$. This pathway was initially described by Kodama, et al. (Kodama, Kl., Nakatani, S., Umehara, K., Shimizu, K., Minoda, Y., and Yamada, K. (1970) Microbial conversion of petrosulfur compounds: Part III. Isolation and identification of products from dibenzothiophene. Agr. Biol. Chem. 34, 1320–1324) and is frequently referred to as the Kodama pathway.

Microbial degradation of organosulfur containing carbonaceous materials by the Kodama pathway, or related pathways involving C—C bond cleavage, is undesirable due to the lack of specificity for sulfur. These nonspecific pathways result in the degradation of structurally related aromatic hydrocarbon compounds thereby greatly reducing the efficiency of the process and the calorific value of the fuel. The lack of sulfur specificity inherent in Kodama like pathways is illustrated by the work of Monticello, et al. (Monticello, D. J., Bakker, D., Schell, M., and Finnerty, W. R. (1985) Appl. Environ. Microbiol. 49, 761–764) who, working with Pseudomonas species, demonstrated that mutants unable to grow on dibenzothiophene were also unable to oxidize naphthalene. It is therefore desirable to utilize a microbial desulfurization process which removes organically bound sulfur via a sulfur specific mechanism without removing carbon from the molecule, thereby operating at an efficiency, and retaining the calorific value of the fuel, in a manner not possible by carbon degradative pathways.

Sulfur specific oxidation of dibenzothiophene by ATCC 39381 resulting in the release of sulfur as sulfate without the degradation of the carbon skeleton is described by Isbister and Doyle (Isbister, J. S., and Doyle, R. C. (Atlantic Res. Corp.) (1985) U.S. Pat. No. 4,562,156). However, the ATCC 39381 culture on deposit does not possess the C-S cleavage trait and the depositors of the culture have stated that the culture on deposit cannot be replaced as such cultures having the C-S cleavage trait to their knowledge do not exist (4th Department of Energy Preparation, Utilization and Environmental Control Contractors Conference, U.S. Department of Energy, Pittsburgh Energy Technology Center, Pittsburgh, Pa. 15236, U.S.A., 1988). More recently, a patent by Kilbane (Kilbane, J. J. (1991) U.S. Pat. No. 5,002,888) describes the use of a mutant strain of *Bacillus sphaericus* strain ATCC 53969 which has the property of sulfur removal from organosulfur compounds by selective cleavage of C—S bonds. In the case of sulfur specific metabolism of dibenzothiophene, the end products are 2-hydroxy bi-phenyl and $SO_4=$. This organism is unable to perform the desulfurization of organosulfur compounds independently, requiring the presence of a "nutritional helper culture". Kilbane and Bielalga have reported the isolation of a mutant strain of *Rhodococcus rhodochrous* strain IGTS8 which performs the identical sulfur specific metabolism of organosulfur compounds but does not require a "helper culture" (Kilbane, J. J. and Bielaga, B. A. (1990) Microbial removal or organic sulfur from coal: a molecular genetics approach. In: Gas, Oil, Coal, and Environmental biotechnology II (Akin, C. and Smith, J. eds.) Institute for gas technology, Chicago, pp. 317–330) van Afferden, et al. (van Afterden, M., Schacht, S., Klein, J. and Truper, H. G. Degradation of dibenzothiophene by Brevibacterium sp. Do. Arch. Microbiol. 153,324–328) reported the isolation of a Brevibacterium species which is able to use dibenzothiophene as a sole carbon, sulfur and energy sources and therefore completely degrades the molecule to $CO_2$ and $H_2O$, this process is initiated by oxidation of the sulfur to dibenzothiophene sulfoxide and then to the sulfone, two intermediates in the proposed pathway utilized by IGTS8. Omori, et al., (Omori, T., Monna, L., Saiki, Y., and Kodama, T. (1992). Desulfurization of dibenzothiophene by Corynebacterium sp strain SY1. Appl. Environ. Microbiol. 58, 911–915) reported the isolation of Corynebacterium sp strain SY 1 which selectively removed sulfur from dibenzothiophene and a number of other organosulfur compounds. Corynebacterium sp strain SY 1 metabolized dibenzothiophene to dibenzothiophene-5-oxide, dibenzothiophene sulfone and hydroxybiphenyl, which was subsequently nitrated to produce at least two different hydroxynitrobiphenyls.

In none of the above cases involving sulfur specific metabolism were sterically hindered organosulfur compounds demonstrated to be substrates for sulfur removal. Further, it is evident that the isolation of organisms capable of sulfur specific metabolism of organosulfur compounds of the type found in carbonaceous materials such as coal and oil is not obvious. This is demonstrated by the work of Kilbane and Bielalga (Kilbane, J. J. and Bielaga, B. A. (1990) Microbial removal of organic sulfur from coal: a molecular genetics approach. In: Gas, Oil, Coal, and Environmental biotechnology II)(Akin, C. and Smith, J. eds.) where three strains of *Rhodococcus rhodochrous* different than the sulfur specific strain *Rhodococcus rhodochrous* IGTS8 and five other Rhodococcus strains were shown to lack sulfur specific metabolism of organosulfur compounds. This evidence and work in our own laboratory shows that sulfur specific metabolism of organosulfur compounds is strain specific and not a general characteristic of any genera or species of microorganisms.

SUMMARY OF THE INVENTION

The present invention is two biologically pure cultures of organic sulfur selective microorganisms, Rhodococcus species ATCC 55309 and 55310 respectively, which have the ability to selectively reduce the organic sulfur content of sulfur containing organic carbonaceous material. The culture have been deposited with the American type culture collection, 12301 Park Lawn Drive, Rockville, Md. 20852 and assigned ATCC numbers 55309 and 55310. The two strains of bacteria claimed herein possesses the same metabolic activity with respect to sulfur and are of the same genus and species but differ in colony morphology.

The ability to selectively remove sulfur from organosulfur compounds present in organic carbonaceous material is based on the sulfur specific metabolism of these bacteria which results in the selective cleavage of carbon-sulfur bonds and the release of sulfur which is detected as sulfate or incorporated into biomass.

In a preferred embodiment of the sulfur is sterically hindered in the organic compounds by the location of groups adjacent to the carbon-sulfur bonds such as in the case of mono and dibeta dibenzo-thiophenes. The ability of these organisms to remove sulfur from organosulfur compounds in which the sulfur in sterically hindered allows for the removal of all classes or organosulfur compounds found in carbonaceous fuels such as coals and oils.

DESCRIPTION OF THE PREFERRED EMBODIMENT

Figure 1:
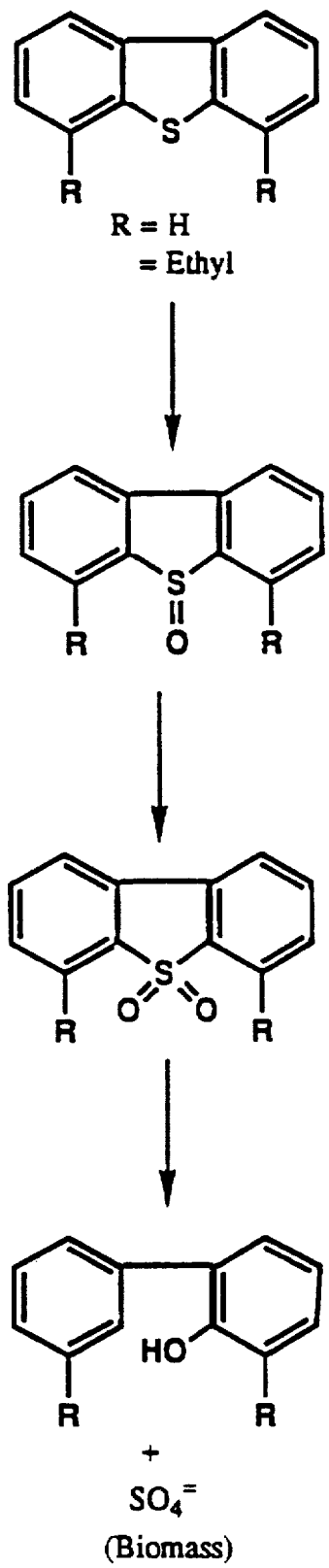
FIG. 1 shows the biochemical pathway for the desulfurization of dibenzothiophene and the sterically hindered derivative 4,6-diethyldibenzothiophene by Rhodococcus species ATCC 55309 and 55310.

The present invention is newly discovered and isolated microorganisms which can effectively and specifically remove sulfur from organic sulfur compounds of the type commonly found in petroleum products, coal, tar sands and shale oil, including those compounds in which the sulfur atoms are sterically hindered. The unique ability of these microorganisms to perform carbon-sulfur bond specific biochemistry on these organic sulfur compounds is the basis for the use of these microorganisms in a process for the selective removal of organic sulfur from fuels and related products.

Microorganisms capable of selective sulfur removal from organic sulfur compounds were isolated from inter tidal marine sediments. This was accomplished by enrichment culture of the sediments employing a growth medium containing a sterically hindered organic sulfur molecule, 4,6-diethyldibenzothiophene (DEDBT) as the sole source of sulfur, and a readily assimilable carbon/energy source (sodium acetate). The formulation of this growth medium was such that organism capable of obtaining their required sulfur from the organic sulfur compound could grow, while the growth of those organisms which could not would be discouraged. The addition of a readily assimilable carbon/ energy source provided those organisms capable of sulfur specific sulfur removal of growth advantage by eliminating the need to obtain both carbon/energy and sulfur from the relatively poor carbon/energy source provided by the organic sulfur compounds.

From such enrichment cultures, two nonsporing Gram-positive irregular rod shaped bacteria were isolated, and identified as Rhodococcus species, which are capable of removing the sulfur from DEDBT, yielding primarily a product lacking sulfur and being monohydroxylated in the position previously occupied by sulfur, namely 2-hydroxy-3, 3-diethyl biphenyl. In addition, the isolated organisms were shown to be able to perform the identical chemistry using dibenzothiophene as the substrate, demonstrating that sulfur removal is not limited to sterically hindered organic sulfur compounds.

Separately, the two organisms were inoculated into 200 ml of a mineral salts/acetate medium containing DEDBT as the sole course of sulfur, in a one liter Eriemeyer flask with a foam rubber stopper. The cultures were incubated on a shaker (200 rpm) at room temperature for seven days. The cultures were acidified to pH3 with HCl and extracted three times with methylene chloride. The organic phases was filtered through anhydrous sodium sulfate and the volume was reduced by evaporation under a stream of $N_2$ gas at room temperature to 0.1 ml.

The above methylene chloride culture extract was analyzed by GC/FID, GC/MS and GC/SCD (sulfur chemiluminescense detection) (FIG. 1), one major product was detected, and identified as 2-hydroxy 3,3-diethyl biphenyl, a sulfur-free derivative of the starting material, with its carbon skeleton intact and a hydroxyl group and a hydrogen atoms inserted in the location previously occupied by the carbon-sulfur bonds. Analysis of the culture extract demonstrates the formation of the sulfoxide and sulfone of the starting organosulfur compound suggesting that these are intermediates in the pathway resulting in sulfur removal. Sulfur is released as $SO_4=$ or assimilated into biomass. The substrate organosulfur compound (dibenzothiophene), intermediate products and final products formed by the desulfurization activity of the two claimed Rhodococcus species (ATCC 55309 and 55310) are shown in FIG. 1.

APPLICATION OF THE MICROBIAL DESULFURIZATION PROCESS

To accomplish the desulfurization of a carbonaceous material either of the claimed organisms, Rhodococcus species ATCC 55309 and 55310 or prepared cell fractions containing the enzymes responsible for desulfurization or the isolated enzymes, are brought in contact with the carbonaceous material (oil, coal, lignite, bitumen, etc.) in a manner sufficient to produce the desired degree of organic sulfur removal. This can be accomplished in such configurations as described below in which the system operates in a batch, semibatch or continuous mode. In all examples the biological system which carries out the desulfurization of organosulfur molecules, whether in the form of whole cells of the organisms Rhodococcus species ATCC 55309 and/or 55310, or prepared cell fractions containing the enzymes responsible for desulfurization or the isolated enzymes, will be referred to below as the biocatalyst.

1 ) A slurry bio-reactor where the biocatalyst is free in an aqueous solution comprising mineral nutrients and an assimilable source of carbon and contacted with the carbonaceous material and where the oxidized sulfur waste is removed from the aqueous phase after separation from the carbonaceous material.

2) A slurry bio-reactor where the biocatalyst, essentially free of non-adhering water is directly contacted with the carbonaceous material and where the oxidized sulfur waste and biocatalyst is removed by washing the carbonaceous material with minimal quantities of water or by solvent extraction or both.

3 ) A fixed bed or slurry bio-reactor in which the biocatalyst is immobilized on a solid support in an aqueous solution comprising mineral nutrients and an assimilable source of carbon and contacted with the carbonaceous material and where the oxidized sulfur waste is removed from the aqueous phase after separation from the carbonaceous material.

4) A fixed bed or slurry bio-reactor in which the biocatalyst is immobilized on a solid support and, essentially free of non-adhering water, contacted with the carbonaceous material and where the oxidized sulfur waste and biocatalyst is removed by washing the carbonaceous material with minimal quantities of water or by solvent extraction or both.

5) A membrane bio-reactor in which the biocatalyst, suspended in an aqueous solution comprising mineral nutrients and an assimilable source of carbon or nonaqueous solution, is separated from the carbonaceous material by a membrane which prevents the mixing of biocatalyst and carbonaceous material while allowing contact at the membrane surface for desulfurization to occur, therefore, obviating the need for separation of product and waste and/or biocatalyst.

We claim:

1. A biologically pure culture of a microorganism having all the identifying characteristics of Rhodococcus species ATCC 55309 or Rhodococcus species ATCC 55310.

2. A biologically pure culture of a microorganism selected from the group consisting of (a) Rhodococcus species ATCC 55309, (b) Rhodococcus species ATCC 55310, (c) a mutant of microorganism (a), and (d) a mutant of microorganism (b), or combinations thereof, wherein mutant (c) and mutant (d) are each capable of removing organic sulfur from a sulfur-containing organic carbonaceous fuel substrate.

3. A process for removing organic sulfur from a sulfur-containing organic carbonaceous fuel substrate containing a dibenzothiophene having sulfur-carbon bonds comprising contacting said substrate with a microorganism of claim 2 which cleaves said sulfur-carbon bonds thereby resulting in removal of said organic sulfur from said substrate.

4. The process of claim 3 wherein said substrate is coal.

5. The process of claim 3 wherein said substrate is selected from the group consisting of petroleum and products thereof.

6. A biologically pure culture of a microorganism having all the identifying characteristics of (a) Rhodococcus species ATCC 55309, (b) Rhodococcus species ATCC 55310, (c) a mutant of microorganism (a), and (d) a mutant of microorganism (b), or combinations thereof wherein mutant (c) and mutant (d) are each capable of removing organic sulfur from a sulfur-containing organic carbonaceous fuel substrate.

* * * * *